(12) United States Patent
Blasco et al.

(10) Patent No.: US 7,871,194 B2
(45) Date of Patent: Jan. 18, 2011

(54) DILUTION APPARATUS AND METHOD

(75) Inventors: Alain Blasco, St. Romain de Jalionas (FR); Gerard Michel, Worcestershire (GB)

(73) Assignee: Malvern Instruments Limited, Worchestershire (GB)

( * ) Notice: Subject to any disclaimer, the term of this patent is extended or adjusted under 35 U.S.C. 154(b) by 269 days.

(21) Appl. No.: 11/871,211

(22) Filed: Oct. 12, 2007

(65) Prior Publication Data

US 2008/0134805 A1 Jun. 12, 2008

Related U.S. Application Data

(63) Continuation of application No. PCT/GB2006/001303, filed on Apr. 12, 2006.

(30) Foreign Application Priority Data

Apr. 12, 2005 (GB) ................... 0507349.9

(51) Int. Cl.
*B01F 3/20* (2006.01)
*B01F 5/00* (2006.01)
*B01F 7/00* (2006.01)
*B01F 13/10* (2006.01)
*B01F 15/02* (2006.01)

(52) U.S. Cl. ................ 366/152.6; 366/163.2

(58) Field of Classification Search ............. 366/152.6, 366/153.1, 163.1, 163.2
See application file for complete search history.

(56) References Cited

U.S. PATENT DOCUMENTS 3,338,560 A * 8/1967 Katzer et al. ................ 366/101

(Continued)

FOREIGN PATENT DOCUMENTS

EP 0911296 4/1999

(Continued)

*Primary Examiner*—Tony G Soohoo
(74) *Attorney, Agent, or Firm*—Baker Botts LLP

(57) ABSTRACT

A dilution apparatus suitable for use with particles suspended in a fluid is described. The apparatus comprises a first batch diluter and a second continuous diluter. The first diluter comprises a vessel having at least one inlet, and an outlet, the at least one inlet being arranged to receive diluent so as to mix said sample with said diluent. The second diluter comprises a sample input, a diluent inlet and an output, the diluent input being arranged such that diluent entering the second diluter experiences a pressure drop. The pressure drop is sufficient to entrain at least a portion of diluted sample from the first diluter through the sample input. The outlet of the first diluter is arranged to be in communication with the input of the second diluter such that a sample that has been pre-diluted in the first diluter is arranged to be further diluted in the second diluter.

16 Claims, 3 Drawing Sheets

U.S. PATENT DOCUMENTS

| | | | |
|---|---|---|---|
| 4,634,560 | A | 1/1987 | Eckert |
| 4,669,889 | A * | 6/1987 | Yamaguchi et al. ...... 366/160.2 |
| 5,054,309 | A | 10/1991 | Mettes et al. |
| 5,090,258 | A | 2/1992 | Yamasaki et al. |
| 5,109,708 | A | 5/1992 | Lawless |
| 5,454,912 | A | 10/1995 | Dougherty |
| 5,676,494 | A | 10/1997 | Ruch |
| 5,857,773 | A * | 1/1999 | Tammelin ................. 366/178.1 |
| 5,895,869 | A | 4/1999 | Von Behrens et al. |
| 5,907,108 | A | 5/1999 | Garcia-Rubio et al. |
| 6,007,235 | A | 12/1999 | Freud et al. |
| 6,211,956 | B1 | 4/2001 | Nicoli |
| 6,286,376 | B1 | 9/2001 | Davidson et al. |
| 6,383,462 | B1 | 5/2002 | Lang |
| 6,416,642 | B1 | 7/2002 | Alajoki et al. |
| 6,425,529 | B1 * | 7/2002 | Reinsch et al. ........... 366/163.2 |
| 7,100,459 | B2 | 9/2006 | Gehner et al. |
| 2005/0185505 | A1 * | 8/2005 | McCurdy et al. ......... 366/153.1 |
| 2007/0036024 | A1 * | 2/2007 | Kubala et al. ............ 366/163.2 |
| 2007/0137314 | A1 | 6/2007 | Watson et al. |

FOREIGN PATENT DOCUMENTS

| | | |
|---|---|---|
| GB | 2028164 | 3/1980 |
| JP | 2006-517665 A | 7/2006 |
| WO | WO 2004/072603 | 8/2004 |

\* cited by examiner

DILUTION APPARATUS AND METHOD

CROSS-REFERENCE TO RELATED APPLICATIONS

This application is a continuation of International Application PCT/GB06/001303, filed Apr. 12, 2006, which claims the benefit of Great Britain Application No. 0507349.9, filed Apr. 12, 2005, each of which is incorporated by reference in its entirety herein.

FIELD OF THE INVENTION

This invention relates to a dilution apparatus and method. More particularly, but not exclusively, it relates to a dilution apparatus and method suitable for use with a particle size characterisation apparatus. Even more particularly, but not exclusively, it relates to a dilution apparatus and method suitable for the dilution of a small volume sample, or a batch sample, to a pre-determined dilution ratio.

BACKGROUND OF THE INVENTION

The use of a multi-stage continuous diluter as a component for sampling and diluting a process slurry for subsequent measurement of particle properties in the dilute state is described in our co-pending International Patent Application PCT/GB2004/000599 (Publication No. WO/2004/072603), the contents of which are incorporated herein by reference.

Such a multi-stage diluter offers a number of advantages over current dilution apparatus, for example it provides a continuously supplied dilute sample representative of the process that is delayed by only a few seconds between sampling and characterisation of the slurry. This allows 'real-time' process control.

Additionally, as sample is drawn through the diluter by a pressure drop in the diluent the diluter does not require pumps or other electrical apparatus to be close to the process, thereby increasing the safety of the diluter where a flammable solvent is used.

Such a diluter is advantageous for processes that are large scale and continuous, for example a pigment milling processes. In such large scale continuous processes the consumption of diluent is small compared to the volume of diluent consumed in the process itself. Also, diluted material can be returned to the process and re-absorbed with little or no impact on downstream product quality.

However, a continuous diluter also has drawbacks when applied to smaller scale or batch processes. For example each stage of a continuous diluter consumes typically 1-2 ltrs/min per stage and will extract approximately 150 mls of sample from the process per minute. With a diluter having from 2-6 stages in typical configurations the consumption of diluent can become a significant problem where it is expensive, toxic or environmentally damaging.

Such a continuous sampling regime can be unsuitable for processes where high volume and continuous consumption of diluent, and sample, are a disadvantage. For example, in small volume and batch processes involving high value material, for example a pharmaceutical, the diluted sample cannot be returned to the process without impacting the downstream processing. This means that either the sample must be discarded, or that the diluted sample requires special recovery means. In either case the cost of sampling the process is increased, and where special recovery means are used the complexity of the sampling arrangement is increased also.

Even in some high volume slurry processes continuous consumption of slurry is also a problem in that material is extracted from the process flow during times when no measurement is required. This means that slurry is being wasted thereby reducing the overall efficiency of the process.

SUMMARY OF THE INVENTION

According to a first aspect of the present invention there is provided a dilution apparatus, suitable for use with particles suspended in a fluid, comprising a first batch diluter and a second continuous diluter;

the first diluter comprising a vessel having at least one inlet, and an outlet, the at least one inlet being arranged to receive a sample to be diluted and the at least one inlet being arranged to receive diluent so as to mix said sample with said diluent;

the second diluter comprising a sample input, a diluent input and an output, the diluent input being arranged such that diluent entering the second diluter experiences a pressure drop, said pressure drop being sufficient to entrain at least a portion of diluted sample from the first diluter through the sample input; characterised in that the outlet of the first diluter is arranged to be in selective communication with the input of the second diluter such that a sample that has been pre-diluted in the first diluter is arranged to be further diluted in the second diluter.

According to a further aspect of the present invention there is provided a dilution apparatus, suitable for use with particles suspended in a fluid, comprising a first diluter and a second diluter;

the first diluter comprising a vessel having at least one inlet, and an outlet, the at least one inlet being arranged to receive a sample to be diluted and the at least one inlet being arranged to receive diluent so as to mix said sample with said diluent in a turbulent mixing regime;

the second diluter comprising a sample input, a diluent input and an output, the diluent input being arranged such that diluent entering the second diluter experiences a pressure drop, said pressure drop being sufficient to entrain at least a portion of diluted sample from the first diluter through the sample input; characterised in that the outlet of the first diluter is arranged to be in selective communication with the input of the second diluter such that a sample that has been pre-diluted in the first diluter is arranged to be further diluted in the second diluter.

The first diluter may be a batch diluter/sampler. The second diluter may be a continuous diluter/sampler.

The term "turbulent mixing regime" is used herein to refer to a mixing regime in which sample is not mixed with diluent by means of entraining the sample in the diluent under the action of a pressure difference within the diluent flowpath.

In embodiments where the first diluter operates in a batch mode, the first diluter can be arranged to pre-dilute the sample into an intermediate vessel, before the pre-diluted sample is diluted further by the second diluter. This has advantages.

The weakness of a continuous diluter (such as the second diluter in isolation) is that a lot of sample (for example slurry) is used. In the present invention, the first diluter can operate in a batch mode, reducing the amount of sample that is needed. This can be advantageous if the sample is in short supply or is expensive, or is toxic. There may be other reasons for conserving sample.

Conversely, the weaknesses of purely a batch sampling approach which does not provide for continuous measurement, and requires wash cycles and subsequent downtime, are overcome by the continuous operation that can be offered by the second diluter. A sample analysing instrument, for example a particle size analyser, effectively sees a continuous operation.

Flexibility can be provided by varying the height of the liquids stored in the vessel of the first diluter, which can be adjusted automatically to match the different behaviours of the first and second diluters. The height of liquid in the batch diluter vessel can be allowed to vary, or controlled to vary, as deemed desirable.

As the first diluter provides a pre-dilution, and the second diluter draws sample from the first diluter, the second diluter requires fewer stages. This results in the use of less diluent than if only a multi-stage diluter is used to achieve the same dilution ratio.

Also, the second diluter can be selectively isolated from a process to be sampled so that further sampling does not take place, thereby reducing the amount of sample extracted from a process in comparison with a continuous sampling arrangement.

Such a construction of sample dilution apparatus offers mediation between the conditions required for the diluter and the process condition. The second diluter operates most efficiently at pressures close to atmospheric and therefore operates best when sampling unpressurised processes. The selective isolation of the second diluter from the process allows sampling of a pressurised process by using the first diluter as a buffer between the process and the second diluter.

The apparatus may comprise a plurality of second diluters arranged in series. The use of a number of second diluters allows a desired dilution to be achieved.

The first diluter may comprise an agitation means. The agitation means may be operable to maintain sample substantially suspended in diluent. The agitation means may comprise a stirrer, typically with a blade at a free end thereof. The agitation means may be driven by a motor. Alternatively, or additionally, the agitation means may comprise an ultra-sonic drive unit. The ultra-sonic drive unit may serve both to assist suspension and promote dispersion by preventing particles aggregating.

The inlet may comprise a sampling valve. The sampling valve may be arranged to selectively extract a sample from a process. This allows the process condition to be variable as it isolates the process, prevents sample extraction from the process from the apparatus at times, and communicates process fluid with the apparatus at times (allows sample extraction at times).

The first diluter may comprise a level sensor arranged to generate a signal indicative of the attainment of a pre-determined volume of liquid in the first diluter. The signal may be arranged to control a valve to selectively place the first diluter in communication with a diluent source.

The signal may be arranged to control the valve such that a substantially constant volume of liquid is maintained in the first diluter. This allows sample to pseudo-continuously flow through a characterisation apparatus to provide a 'rolling integration' of sample characteristics over a number of sampling periods, when the diluted sample is later used for sample characterisation.

Alternatively, the signal may be arranged to control the valve such that diluent is prevented from entering the first diluter once the pre-determined volume of liquid is attained. This allows batch operation of the apparatus, whereby a known pre-dilution ratio is achieved prior to diluting the sample in the second diluter.

Furthermore, this can represent a way in which the first and second diluters can be run continuously, and ensure that the two samplers are in lockstep. This can overcome some of the problems associated with systems that use only continuous sampling or only batch sampling. Providing a batch sampling element as the first diluter before a continuous sampling element as the second diluter, with the level of liquid in the batch mode rising and falling to adjust automatically permits continuous use of a batch mode sampler, and also allows use of a continuous diluter without excess use of sample, for example slurry.

The signal may be arranged to control the valve so as to maintain the sample fluid volume in the first diluter between an upper and a lower amount. Alternatively or additionally some other characteristic of the fluid may be kept within bounds (e.g. its pressure at the outlet of the first diluter, or at some point in the first diluter). The signal may be arranged to control the valve such that diluent enters the first diluter between sampling of a process. The first diluter may comprise a diluent director arranged to direct diluent input into the vessel. The diluent director may be arranged to direct diluent onto a wall of the vessel. This allows the vessel to be washed down to remove particles that have settled onto the walls of the vessel, thereby reducing cross-contamination between process samplings.

The first diluter may comprise a tapered, e.g. frusto-conical, end portion adjacent the outlet. The end portion may be have a steep angle of inclination, for example in excess of approximately 30° and preferably approximately 60° or more. The end portion may be substantially free from substantially horizontal ledges. The use of a smooth steep sloping, e.g. frusto-conical, end portion reduces the opportunities for sample particulates to settle out of suspension and remain in the diluter, contaminating the diluter for the subsequent sampling, and also potentially biasing results.

The outlet may comprise a filter, typically a sieve. The use of a filter in the outlet reduces the likelihood of a large particle entering the second diluter which may comprise fine bore pipes that may become blocked by such a large particle.

The vessel may be arranged to receive diluent from either, or both, of a diluent inlet or/and the second diluter. The second diluter may be arranged to backfill when the output is selectively closed.

The outlet of the first diluter may be arranged to be in selective communication with the input of the second diluter.

According to a second aspect of the present invention there is provided a method of sample dilution, suitable for use with particles suspended in a fluid, comprising the steps of:
(i) pre-diluting a sample in a vessel by the mixing of the sample and a diluent in a batch diluter; and
(ii) continuously entraining at least part of the sample pre-diluted in step (i) into a flow of diluent.

According to a further aspect of the present invention there is provided a method of sample dilution, suitable for use with particles suspended in a fluid, comprising the steps of:
(i) pre-diluting a sample in a vessel by the mixing of the sample and a diluent in a turbulent mixing regime; and
(ii) entraining at least part of the sample pre-diluted in step (i) into a flow of diluent.

According to a third aspect of the present invention there is provided a particle characterisation apparatus comprising a dilution apparatus according to the first or second aspect of the present invention, a cell (optionally) in selective communication with the output of the second diluter, a sensor, a signal source arranged to generate a sensing signal, and a processor;
the cell comprising a window arranged to be at least partially transmissive to the sensing signal generated by the signal source;

the sensor being operatively located relative to a further, or the, window arranged to be at least partially transmissive to a characteristic signal indicative of a characteristic of a component of a sample arranged to pass through the cell, the characteristic signal being generated from the interaction of the sensing signal with the component of the sample;

the sensor being arranged to sense the characteristic signal and to pass an output signal to the processor; and the processor being arranged to process the output signal to recover a measurement of the characteristic of the sample.

The apparatus may comprise an input valve arrangement between the output of the second diluter and the cell. The valve arrangement may be arranged to selectively direct diluted sample from the output of the second diluter, or diluent, through the cell. The sensor may be arranged to capture background measurements whilst only diluent passes through the cell.

The valve arrangement may be arranged to direct diluent to either, or both, of the diluent inlet or, and, the output of the second diluter. The valve arrangement may be arranged to direct fluid output from the second diluter to waste, or to a reclamation apparatus, following the end of a measurement.

The processor may be arranged to control the valve arrangement so as to allow the flow of fluid from the output of the second diluter to the cell whilst sample is detected in the fluid by the sensor.

The cell may comprise two substantially parallel windows opposing one another. The source may be adjacent one of the windows and the sensor may be adjacent the other of the windows. This arrangement is suitable for forward scattering measurements.

The source and the sensor may be adjacent the same window, or windows adjacent each other. This arrangement is suitable for backscattering measurements.

The processor may be arranged to generate an indicator signal should the measured characteristic of the sample lie at least partially outside a pre-determined threshold value. The indicator signal may trigger an alarm to a user of the apparatus. The indicator signal may be arranged to stop the process being monitored. The indicator signal may be passed to an automated process controller, the controller being arranged to vary process parameters in response to the indicator signal.

The processor may be arranged to recover a particle size distribution of the sample.

According to a further aspect of the invention, there is provided a dilution apparatus suitable for use with particles suspended in a fluid, comprising a first diluter and a second diluter in fluid communication with the first diluter, wherein the first diluter is a batch diluter and the second diluter is a continuous diluter.

According to another aspect of the invention, there is provided a method of determining a particle size distribution of particles in a fluid comprising diluting the fluid prior to analysing the particle size distribution, diluting the fluid comprising diluting a batch sample of fluid taken from a process and batch diluting it in a batch diluter, and taking the output of the batch diluter and entraining it in a flow of diluent of a continuous diluter, passing the output of the continuous diluter directly or indirectly to a particle size distribution analyser, and analysing the particle size distribution using the analyser.

In the method:
(i) the sample may be batch diluted a plurality of times prior to being continuously diluted; or
(ii) the sample may be batch diluted before and after at least one continuous dilution process; or
(iii) the sample may be continuously diluted in a plurality of successive dilution stages1 or
(iv) the sample may be continuously diluted before and after a batch dilution process; or
(v) any combination of these options (i) to (iv) may take place.

The sample may be a sample of a production process intended to produce a product with a predetermined particle size distribution, and the method may be performed in order to determine that the product does have a particle size distribution that is within acceptable limits. The method may be performed using on-line samples from the production process whilst the production process is operating, and feedback on the product may be provided whilst the process is operating. Alternatively, the method may be performed off-line on a sample.

BRIEF DESCRIPTION OF THE DRAWINGS

The invention will now be described, by way of example only, with reference to the accompanying drawings, in which.

DETAILED DESCRIPTION OF THE INVENTION

Figure 1:
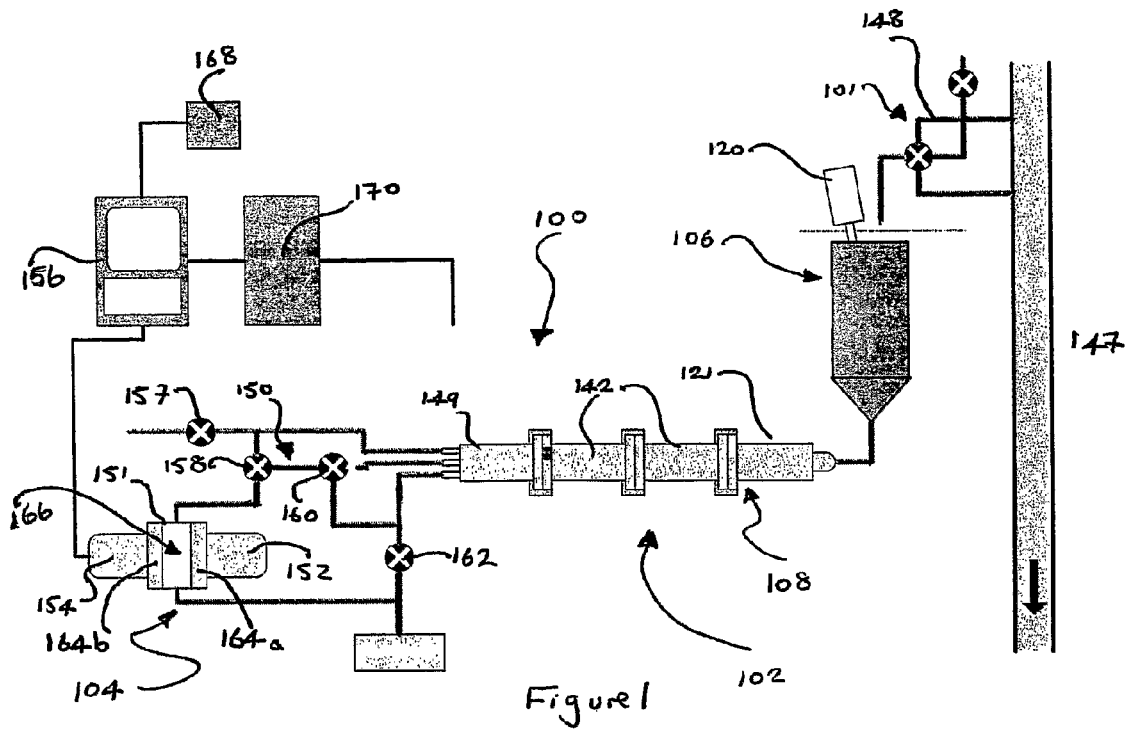
FIG. 1 is a schematic diagram of an embodiment of a particle characterisation apparatus according to an aspect of the present invention comprising an embodiment of a dilution apparatus according to another aspect of the present invention.
Figure 2:
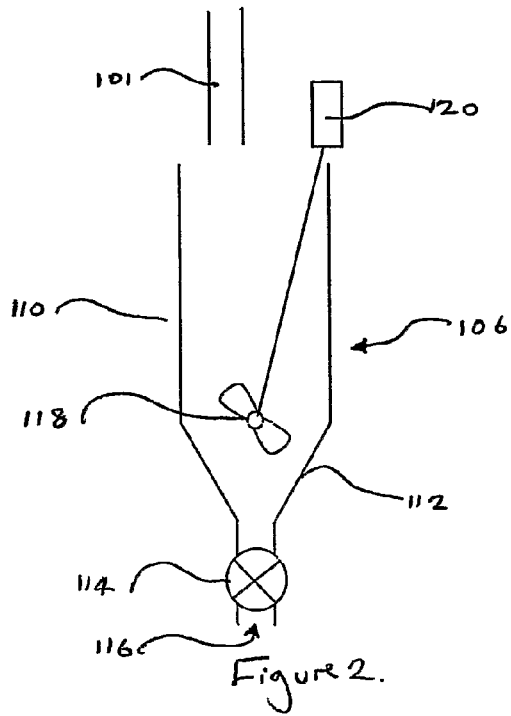
FIG. 2 is a schematic diagram of a turbulent diluter forming a component of the dilution apparatus of FIG. 1.
Figure 3:
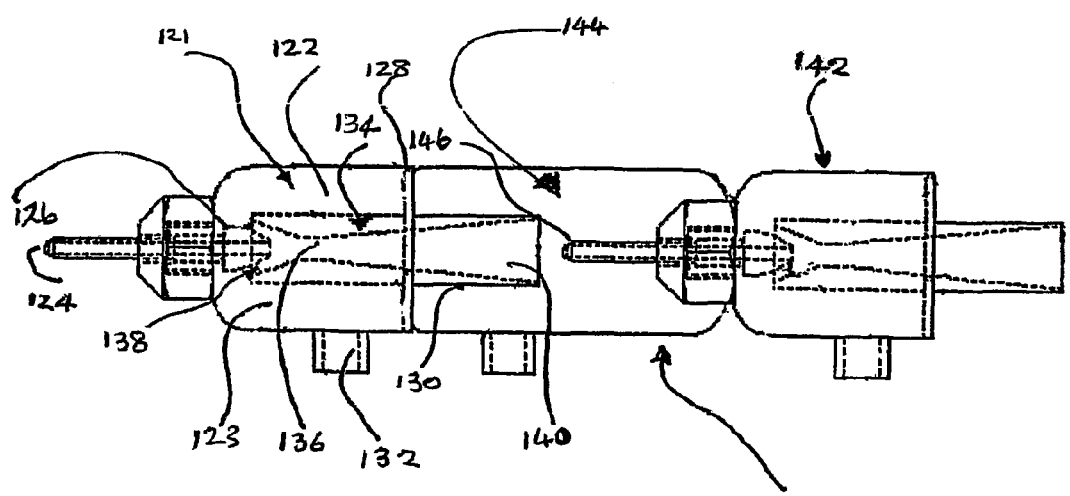
FIG. 3 is a schematic diagram of a stage of a continuous diluter forming a component of the dilution apparatus of FIG. 1.

Referring now to FIGS. 1 to 3, a particle characterisation apparatus 100 comprises a sample inlet arrangement 101, dilution apparatus 102 and a characterisation unit 104.

The dilution apparatus 102 comprises a pre-dilution turbulent diluter 106 and a multi-stage continuous diluter 108. The turbulent diluter 106 comprises a predilution vessel 110 having a substantially circular cross-section and terminating at a lower end in a frusto-conical end portion 112. The predilution vessel 110 typically has a volume of between 200 ml and 1 l. The end portion 112 has a valve 114 at an output 116 of the vessel 110. A stirrer 118 is located within the vessel 110, and is powered by a motor 120.

The continuous diluter 108 comprises a sampler probe 121 having a cylindrical housing 122. The housing 122 typically has an internal diameter of 10 mm and a cavity 123 having a typical length of 50 mm. The housing 122 is connected to a sample inlet 124 at one end of the housing 122. The inlet 124 is connected to the output 116 of the predilution vessel 110. The sample inlet comprises an introducer tip 126 having a tapered head section, tapering toward the point of sample discharge into the housing 122.

The shape of the introducer tip 126 and a mouth of the housing 122 are substantially complementary in shape. Their shapes are variable in order to optimise the pressure drop experienced at the introducer tip 126 during operation. Additionally, a collet lock 128 allows minor adjustments in the positioning of the tip introducer 126 to be made.

A mixing conduit 130 extends outwardly from the housing 122 at an opposite end of the housing 122 to the inlet 124. The conduit 130 is arranged such that diluent entering the cavity 123 through a diluent inlet 132 passes out of the sampler probe 121 either via the sample inlet 124 or a fluid outlet 134. The mixing conduit 130 has a throat section 136 and a mouth portion 138 into which the sample introducer tip 126 is partially inserted. The throat section 136 typically has a diameter of 3 mm and the mouth portion 138 typically has a diameter of 8 mm. The mouth portion 138 tapers down to the throat section 136. The throat section 136 is succeeded by a divergent portion of tube 140, which provides a flow path to the fluid outlet 134.

The sampler probe 121 is connected to a diluter unit 142. A free end of the conduit 130 locates in a cylindrical bridge unit 144 such that the fluid outlet 134 is in communication with an inlet 146 of the diluter 142. Typically, the bridge unit 144 is connected by respective screw fittings to both the probe 121 and the diluter unit 142. This allows the position of the fluid outlet 134 of the probe 121 to be adjusted with respect to the sample inlet 146 of the diluter unit 142.

The diluter unit 142 is substantially of the same construction as the sampler probe 121. In a preferred embodiment a number of diluter units are connected together in series and the final dilution ratio of the sample is dependent upon the number of diluter units connected together.

In use, the sample inlet arrangement 101 is arranged to input sample extracted from a process flow in a process pipe 147 and mixed with diluent into the turbulent diluter 106. A valve arrangement 148 is arranged to mix the sample with the diluent in a first open position. The valve arrangement 148 typically terminates in a jet coaxial with the vessel 110. Typically, the valve arrangement 148 is arranged such that the extraction of sample from the process pipe 147 has little impact upon the process flow and the valve arrangement 148 is arranged to be bypassed by the process flow when not sampling.

The volume of the valve arrangement 148 is typically exact and known, typically between approximately 1 ml and 4 ml, so that an exact volume of process sample, typically a slurry, is taken during the sampling process. However, it will be appreciated that the volume of the sample extracted via the valve arrangement will vary dependent upon the application for which the diluter is being used.

The valve arrangement 148 isolates the dilution apparatus 100 from the process pipe 147. This allows the sampling of high or low pressure processes to be conducted in conjunction with the use of a continuous diluter, which typically operates optimally at, or close to, atmospheric pressure.

The valve arrangement 148 can be configured in a second open position such that diluent washes through the valve arrangement 148 without sampling extracting a process sample from the process pipe 147. This is useful in order to ensure that substantially all the process sample extracted from the process pipe 147 is washed into the turbulent diluter 106. The valve can also be closed to prevent the passage of both diluent and sample into the vessel 110.

The turbulent diluter 106 can be partially pre-filled with diluent either via valve arrangement 148 or from another diluent source (not shown). Alternatively, the turbulent diluter 106 can be filled via the valve arrangement 148 following the extraction of the process sample from the process pipe 147. It will usually be preferable to partially pre-fill the turbulent diluter 106 with diluent from whatever sources of clean diluent are available. This is because the rate of continuous measurement is limited by the fill and empty rate of the turbulent diluter.

The pre-diluted sample is maintained in suspension by the stirrer 118. The vessel 110 may be filled and emptied with each process sample extracted from the process pipe 147. The apparatus is designed to ensure that all the sample is observed by the characterisation unit 104 in a single measurement. However, such an approach requires the stirrer 118 to be stopped at the point where the level of the pre-diluted sample approaches the level of impeller blades of the stirrer 118. This is in order to avoid cavitation inducing bubbles in the sample, which will influence measurements taken in the characterisation unit 104.

Alternatively, the apparatus 100 can be operated so that a measurement is timed to occur during the passage of one process sample and its diluent through the dilution apparatus 102, a sub-sampling approach. A sub-sampling approach typically involves measuring a particle characteristic from only a fraction of the process sample (instead of all of the sample, which is also possible). For example, where dense particles require continuous agitation by a stirrer to prevent sedimentation the stirrer will cause bubbles to be introduced into the sample as the diluent level drops to the level of the stirrer blades. This is undesirable as bubble result in spurious particle characteristic measurements. Therefore the process sample is sub-sampled by terminating measurement of the particle characteristic prior to the diluent level reaching the level of the stirrer blades in order to reduce the possibility of measuring the characteristics of bubbles.

When using the sub-sampling approach sample characterisation measurements end whilst sample still flows through the characterisation unit 104, or the characterisation unit 104 can attempt to measure all of the contents of the vessel 110 by waiting until the vessel 110 is as close to being drained completely as is possible, without risking the entrainment of air into the continuous diluter 108.

Upon completion of a sample characterisation measurement the vessel 110 is in any case left to run till empty. At this point a defensive wash of the vessel's walls can be carried out with clean diluent. The defensive wash will result in the wash diluent and any particles retained from the previous sample to be washed through to the waste. The necessity of a defensive wash is typically determined by the speed of operation and the prevalence of the sample to settle out of suspension. It makes the washing more efficient when the diluent inlet was constructed as a coaxial jet that washed the walls of the tank as well as introducing the diluent.

In some circumstances, the defensive wash may be processed after it has left the apparatus to reclaim its content particles. Sometimes this may involve simply adding the wash to the fluid from which samples are taken. Other times (e.g. in the pharmaceutical industry) this would be inappropriate and a separate reclamation process may be envisaged. Of course, the wash can simply be disposed of as waste.

Process sample can be added to the vessel 110, as the vessel 110 is continuously having fresh diluent added thereto. Thus, the vessel 110 acts as a time averaged integrator of process conditions over time. More particularly any portion of the process sample has an average residence time in the vessel 110. The diluted sample leaving the tank represents a time average of the process condition over the period of the average residence time. However, the diluted sample is available continuously to the characterisation unit 104, allowing for a "sliding integral" style measurement of the samples characteristics.

The diluted sample suspension in the turbulent diluter 106 is drawn through the valve 114 and into the continuous diluter 108 when the valve is open by a pressure drop at the introducer tip 126 of the sampler probe 121 induced by the flow of diluent through from the inlet 124 to the outlet 134 of the probe 121. It is this flow of diluent through the sampler probe 121 that entrains sample from the turbulent diluter 106, as described hereinbefore. The dilute sample mixes with the diluent flowing through the probe 121 and is further diluted by the diluent.

The probe's outlet 134 is in communication with the diluter unit's inlet 146 as noted hereinbefore and the dilute sample is drawn into the diluter unit 142 by the pressure drop at the sample introducer tip. The sample is further diluted in the diluter unit 142 in the same manner as described in relation to the sampler probe 121. In the specific embodiment shown in FIG. 1 there are two diluter units 142 connected in series with an output coupling 149 that couples the continuous diluter 108 to the characterisation unit 104.

The total dilution factor of the process sample upon exiting the dilution apparatus 102 is the product of the dilution ratio experienced by the sample in the turbulent diluter 106 and the ratio due to the continuous diluter 108. The overall dilution ratio of the process sample due to the continuous diluter 108 is dependent upon the number of diluter units 142 employed in the continuous diluter 108 and a number of other factors, for example diluent flow rate.

The characterisation unit 104 comprises an input valve arrangement 150, a cell 151, a radiation source 152, a sensor 154 and a processor unit 156, typically a PC.

The input valve arrangement 150 comprises a diluent inlet valve 157, a routeing valve 158, a continuous diluter outlet valve 160, an waste valve 162. The diluent inlet valve 157 allows the flow of diluent into the continuous diluter 108 via a diluent inlet of the outlet coupling 149, when open, and prevents such a flow when closed.

When the routeing valve 158 is in a first open position it allows the flow of diluent through the cell 151 when the diluent inlet valve 157 is open. This is useful for the purging of the cell 156 between sample characterisation measurements, thereby reducing the cell's susceptibility to window contamination. Such an arrangement also allows background measurements to be taken before every sample characterisation measurement.

The routeing valve 158 can be employed in a second open position with the diluter outlet valve 160 to allow the flow of diluent into the cell 151. When the routeing valve 158 is closed, or in its second open position diluent flows directly to the inlet of continuous diluter 108, subject to the diluent inlet valve 157 being open.

The continuous diluter outlet valve 160 regulates the flow of diluted sample output from an output of the output coupling 149 either into the cell 151, via the routeing valve 158, or to waste/process return feed via the waste valve 162. The latter typically being the case when the cell 151 is purged or background measurements are taken between sample characterisation measurements.

Typically the processor unit 156 is connected to and controls both the radiation source 152 and the sensor 154.

The particle size distribution may be evaluated using known equipment, for example laser diffraction equipment using diffraction theory (e.g. Mie or Fraunhoffer, or developments thereof). Our own MASTERSIZER™ laser diffraction particle size distribution analyser is, of course, suitable.

The radiation source 152 typically emits light at visible wavelengths but may emit radiation (typically coherent) at any wavelength, such as infra-red or ultra-violet wavelengths if appropriate. Additionally, or alternatively, the source may emit other radiation such as acoustic (pressure) waves. The cell 151 has opposing parallel windows 164a,b that form a sample region 166. The windows 164a,b are substantially transparent to the wavelengths emitted by the radiation source 152. Radiation emitted by the radiation source 152 passes through the window 164a into the sample region 166 where it interacts with, and is forward scattered by, the diluted sample passing through the cell 151. A fraction of the scattered radiation passes through the window 164b adjacent the sensor 154. The sensor 154 measures the scattered radiation passing through the window 164b and generates an output signal dependent upon the scattered radiation incident upon it.

In the case of background measurements diluent is passed through the sample region 166 and the sensor 154 generates an output signal based upon the radiation incident upon it without the presence of the diluted sample in the diluent.

The output signal is passed to the processor unit 156 where it is mathematically processed using an analysis programme, to extract information regarding the process condition of particulates.

The processor unit 156 may run a master control programme as a separate task that acts as the overall user interface during normal process operation.

This master control programme typically runs the instrument software as an "driver" using the OPC protocol.

This master control programme provides application dependant functionality and a simple control user interface. This allows process specifications to be tested and, for example, traffic light control where a technician is given a colour coded indication of the state of the process. The results of the measurements can be tested against the specifications by the master control programme and the resultant information provided on a display of the processor unit 156 for operator use. Alarms and failure conditions can also be handled at the master control programme level using the information reported from the sensor 154 and processor unit 156. The results can also be sent to any master data historian/control 168 system using standard protocols.

The master control programme typically connects to an automation cabinet 170 that interfaces all sampler controls to the processor unit 156 in order to provide the valve sequence control. This automation cabinet 170 employs standard off the shelf parts suitable for the application.

The automation cabinet 170 is configured to fail safe and a master control programme operator interface includes a programmed emergency shut down procedure that aborts the process in the event of the process running outside of predetermined threshold conditions. The emergency shutdown procedure is designed to bring the process to a safe quiescent condition.

Although described with reference to forward scattering of radiation it will be appreciated that a radiation source and sensor both located externally and adjacent the same window to effect backscattering sample characterisation measurements with ease. In order to carry out such a backscattering measurements the cell may provided with only a single transmissive window.

Figure 4:
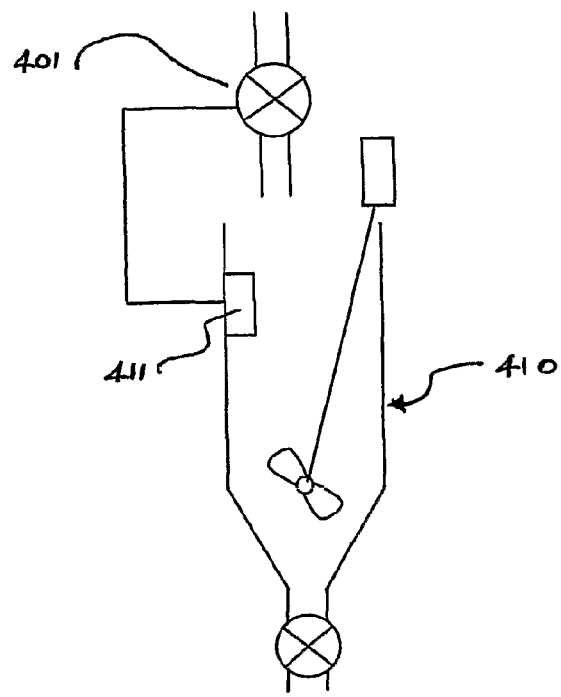
FIG. 4 is a schematic diagram of a vessel and inlet arrangement of an alternative embodiment of a dilution apparatus according to an aspect of the present invention.

Referring now to FIG. 4, in an alternative embodiment a turbulent diluter vessel and sample inlet arrangement are substantially as hereinbefore described with reference to FIG. 1 accordingly corresponding features are accorded similar reference numerals in the four hundred series. The vessel 410 comprises a level sensor 411. The level sensor 411 is connected to and controls the sample inlet arrangement 401 so that diluent is supplied to the vessel 410 in order to maintain the level of suspension in the vessel approximately at a predetermined. This allows a pseudo-continuous measurement ability. A process sample from the process is periodically extracted from the process and is introduced into the vessel 410.

In this mode of operation there is always diluted sample flowing through a sample characterisation unit. Typically, the maximum rate of measurement that can be achieved is approximately once every 5 seconds.

A variant is to keep the level of liquid in the vessel between an upper and a lower permissible level (e.g. re-fill the vessel 410 to the upper level when the liquid gets as low as the lower level).

If the vessel 410 requires a significant time, for example 1 minute, to fully drain the apparatus will provide a rolling integration of all the measurements of characteristics sample injected over the most recent vessel 410 fill and drain cycle times. The instrument is thus able to produce every 5 seconds a result based on a sample averaged over several minutes. Such an apparatus can run continuously and does not require synchronisation with the sampler. The frequency of extraction of the process sample can be adjusted to provide a course concentration adjustment so that the complete diluter system can be readily adapted on site for any application by appropriate choice of diluter stages, set-up and sampling frequency. Coarse, or first stage, dilution can be done at the first diluter (batch) and further dilution at the second, continuous diluter stage: a batch pre-dilution which feeds into a continuous diluter.

Figure 5:
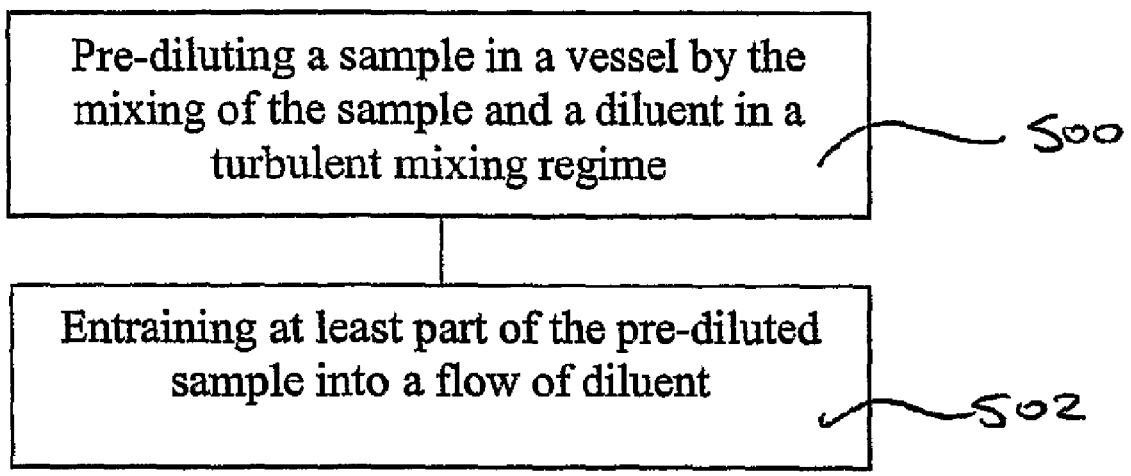
FIG. 5 is a flow diagram detailing the steps of a method of dilution according to an aspect of the present invention.

Referring now to FIG. 5, a method of sample dilution, suitable for use with particles suspended in a fluid, comprise pre-diluting a sample in a vessel by the mixing of the sample and a diluent in a turbulent mixing regime (Step 500) and entraining at least part of the pre-diluted sample into a flow of diluent (Step 502).

Looked at in another way, one aspect of the invention comprises a method of determining a particle size distribution of particles in a fluid comprising diluting the fluid prior to analysing the particle size distribution, diluting the fluid comprising diluting a batch sample of fluid taken from a process and batch diluting it in a batch diluter, taking the output of the batch diluter and entraining it in a flow of diluent of a continuous diluter, passing the output of the continuous diluter directly or indirectly to a particle size distribution analyser, and analysing the particle size distribution using the analyser.

Thus the method can operate by taking batch samples from whatever it is that is to be sampled, rather than requiring a continuous sample of the material to be sampled. This can be advantageous in certain circumstances. For example, the pressure in a production process may be incompatible with the pressure needed as part of the dilution process, making it very difficult to have a permanent, continuous, open link/channel between the two.

There may be more than one batch dilution operation. There may be more than one continuous dilution operation. The batch and/or continuous dilution operations may be chained. They may also be interleaved, or consecutive, or both.

In some embodiments of the invention the sample is obtained from a fluid that is part of a production process that is producing product (e.g. a pharmaceutical, or a pigment, or some other product), where the product needs to have a pre-determined particle side distribution (at least at that stage of the production process), and the method is performed in order to determine that the product does indeed have a particle size distribution those within acceptable limits. There may be feedback controlled to the production process and/or an alarm. The method may be performed as part of a quality control system. Feedback signals from the method may alert users, alert control computers, or indeed in extreme circumstances even close down the production process, or indicate that the product has been produced is unsuitable for use.

The sample may be taken on-line during the production process, with real time feedback (feedback whilst the production process is still operating/information produced while the production process is still operating). Alternatively and/or additionally these analysis/dilution/followed by analysis may be performed off-line of the production process.

The invention claimed is:

1. A dilution apparatus for particle characterization, suitable for use with particles suspended in a fluid, comprising a first batch diluter and a second continuous diluter;
   the first diluter comprising a vessel having at least one inlet, and an outlet, the at least one inlet being arranged to receive a sample to be diluted and the at least one inlet being arranged to receive diluent so as to mix said sample with said diluent;
   the second diluter comprising a sample input tube, a housing having a diluent input and a mixing conduit having a first end which is within the housing and into which the sample input tube is partially inserted, and a second end extending outwardly from the housing to form an output, the mixing conduit having a throat section between the first and second ends; and
   the outlet of the first diluter being arranged to be in communication with the sample input tube of the second diluter such that a sample that has been pre-diluted in the first diluter is arranged to be further diluted in the second diluter.

2. An apparatus according to claim 1, comprising a plurality of second diluters arranged in series.

3. An apparatus according to claim 1, wherein the first diluter comprises an agitator for agitating fluid within the first diluter.

4. An apparatus according to claim 3, wherein the agitator is operable to maintain sample substantially suspended in diluent.

5. An apparatus according to claim 1, wherein the inlet comprises a sampling valve.

6. An apparatus according to claim 5, wherein the sampling valve is arranged to selectively extract a sample from a process.

7. An apparatus according to claim 1, wherein the first diluter comprises a level sensor arranged to generate a signal indicative of the attainment of a pre-determined volume of liquid in the first diluter.

8. An apparatus according to claim 7, wherein the level sensor is arranged to output said signal to control a valve arranged to selectively place the first diluter in communication with a diluent source, in response to said signal.

9. An apparatus according to claim 8, wherein the level sensor and the valve are arranged to operate such that a substantially constant volume of liquid is maintained in the first diluter.

10. An apparatus according to claim 8, wherein the level sensor and the valve are arranged to operate such that diluent enters the first diluter between sampling of a process.

11. An apparatus according to claim 1, wherein the first diluter comprises a frusto-conical end portion adjacent the outlet.

12. An apparatus according to claim 11, wherein the end portion is substantially free from substantially horizontal ledges.

13. An apparatus according to claim 1, wherein the outlet comprises a filter.

14. An apparatus according to claim 1, wherein the vessel is arranged to receive diluent from either, or both, of a diluent inlet and the second diluter.

15. An apparatus according to claim 1, wherein the second diluter comprises means to close the output thereof to backfill the second diluter.

16. An apparatus according to claim 1, comprising means for selectively placing the outlet of the first diluter in communication with the input of the second diluter.

* * * * *